(12) United States Patent
Eggenberger et al.

(10) Patent No.: US 9,031,643 B2
(45) Date of Patent: May 12, 2015

(54) METHOD FOR MONITORING AND COMMUNICATING BIOMEDICAL ELECTROMAGNETIC FIELDS

(71) Applicant: International Business Machines Corporation, Armonk, NY (US)

(72) Inventors: Christian Eggenberger, Wil (CH); Esther Hietler, Vienna (AT); Peter K. Malkin, Ardsley, NY (US); Paul T. Sorenson, Sheboygan, WI (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/087,266

(22) Filed: Nov. 22, 2013

(65) Prior Publication Data
US 2014/0145859 A1 May 29, 2014

Related U.S. Application Data

(62) Division of application No. 12/132,200, filed on Jun. 3, 2008, now Pat. No. 8,594,772.

(51) Int. Cl.
A61B 5/00 (2006.01)
A61B 5/024 (2006.01)
A61B 5/11 (2006.01)

(52) U.S. Cl.
CPC ............. *A61B 5/0004* (2013.01); *A61B 5/0006* (2013.01); *A61B 5/02405* (2013.01); *A61B 5/02438* (2013.01); *A61B 5/1112* (2013.01); *A61B 5/743* (2013.01)

(58) Field of Classification Search
None
See application file for complete search history.

(56) References Cited

U.S. PATENT DOCUMENTS

| 5,283,523 | A | 2/1994 | Uhl et al. |
| 5,444,373 | A | 8/1995 | Johnson et al. |
| 5,579,241 | A | 11/1996 | Corby et al. |
| 6,083,248 | A | 7/2000 | Thompson |
| 6,735,460 | B2 | 5/2004 | Tsukada et al. |
| 6,961,605 | B2 | 11/2005 | Suzuki et al. |
| 7,123,952 | B2 | 10/2006 | Nakai et al. |
| 7,187,960 | B2 | 3/2007 | Abreu |

(Continued)

FOREIGN PATENT DOCUMENTS

| WO | WO03/096893 A1 | 11/2003 |
| WO | WO2007/051889 A1 | 5/2007 |

OTHER PUBLICATIONS

Hart, "Biomagnetometry: imaging the heart's magnetic field", Br Heart J, 1991, 661-62, 65.

(Continued)

*Primary Examiner* — Paula J Stice
(74) *Attorney, Agent, or Firm* — Scully, Scott, Murphy & Presser, P.C.; Daniel P. Morris, Esq.

(57) ABSTRACT

The present invention provides a system and a method of monitoring and communicating biomedical data to a remote receiver. Specifically, the present invention provides a system and method that can monitor a biomedical-based electromagnetic field, e.g., heart rate variability (HRV) field, emitted from a human user ("sender"), and/or communicate the biomedical-based electromagnetic field to a remote receiver by measuring the biomedical-based electromagnetic field emitted from the sender, creating an electronic signal corresponding to the field and transmitting or broadcast and/or apply the signal to a remote receiver.

8 Claims, 9 Drawing Sheets

(56) References Cited

U.S. PATENT DOCUMENTS

| | | | |
|---|---|---|---|
| 7,188,151 | B2 | 3/2007 | Kumar et al. |
| 2001/0051787 | A1 | 12/2001 | Haller et al. |
| 2002/0173928 | A1 | 11/2002 | Willner et al. |
| 2004/0147814 | A1 | 7/2004 | Zancho et al. |
| 2005/0211784 | A1 | 9/2005 | Justin |

OTHER PUBLICATIONS

Bison et al., "Dynamical mapping of the human cardiomagnetic field with a room-temperature, laser-optical sensor", Optics Express, 2003, 904-909, 11-8.

Anonymous, "Global Coherence Monitoring System TM", IHM Newsletter, vol. 6, No. 2, Summer 2007, pp. 1-7.

Shin, "Call centers want to feel your pain. Emotion detection aims to find out how customers are feeling", The Washington Post, Oct. 19, 2006, p. 34.

Tucek, "Traditional oriental music therapy—a regulatory and relational approach", in Music Therapy Today, vol. VII (3), Oct. 2006, pp. 623-647.

Everding, "Research casts doubts on voice-stress lie detection technology", Washington University in St. Louis News & Information, Feb. 10, 2004, http://news-info.wusti.edu/news/page/normal/669.html, p. 1.

Johnson, "Lie-detector glasses offer peek at future of security", Electronic Engineering Times, Jan. 19, 2004, pp. 1-2.

McCraty, "The Energetic Heart: Bioelectromagnetic Interactions Within and Between People", Institute of HeartMath, 14700 W. Park Ave., Boulder Creek, CA 95006, 2003, pp. 1-20.

Magnussen, "Noise Field Research Summary", EMX Corporation, Jun. 1999, pp. 1-80.

Yang, "Modeling and Decomposition of HRV signals with Wavelet Transforms", IEEE Engineering in Medicine and Biology, Jul./Aug. 1997, pp. 17-22.

McCraty et al., "The Electricity of Touch: Detection and measurement of cardiac energy exchange between people", Edited by K.H. Pribram and Mahwah, New Jersey: Lawrence Eribaum Associates, Publishers, 1998, pp. 1-14.

METHOD FOR MONITORING AND COMMUNICATING BIOMEDICAL ELECTROMAGNETIC FIELDS

RELATED APPLICATIONS

This application is a divisional of U.S. application Ser. No. 12/132,200, filed Jun. 3, 2008, which is now U.S. Pat. No. 8,594,772.

FIELD OF THE INVENTION

The present invention generally relates to the communication of biomedical data. Specifically, the present invention recognizes a system and method that can monitor, detect, communicate and/or apply a biomedical-based electromagnetic field, e.g., heart rate variability (HRV) field, emitted by a human user to a remote receiver.

BACKGROUND OF THE INVENTION

Online communication has become increasingly popular, both for entertainment and for business. Such communication includes both asynchronous communication, like email, and synchronous communication, such as Instant Messaging or Chat. Further, these communications include those between only two users (e.g., an email message from a manager to an employee, or an instant message from a husband to a wife), as well as those between larger sets of users (e.g., messages sent to multiple recipients, like a newsletter sent to all club members; or an online chat group, which includes three or more participants). Currently available communication methods allow for the broadcast of information (e.g., text and voice) as well as multimedia data (e.g., live video broadcasts of all of the participants in a teleconference). However, none of the currently available methods includes a broadcast or apply of the biomedical electromagnetic fields of the participants to the other participants.

A method of enabling machine learning to be applied to the magnetic fields emitted by a human heart has been known. However, the method does not provide any means of broadcasting or transmitting these fields to a remote user.

A system that provides a possibly miniaturized device that is able to measure the magnetic fields emitted by the heart has been known. However, the system does not provide any means of broadcasting or transmitting these fields to a remote user.

A method and system that can detect a body condition, (e.g., heart beat rate) and communicating it to a computer have been known. However, the method. The method and system do not, however, provide a method of transmitting the electromagnetic field of one user and then applying it to a remote user.

A contact-less device that can measure the electromagnetic fields generated by a given user's heart has been known. However, the device does not provide any means of broadcasting or transmitting this data to a remote user.

A means of comparing the physical condition of two or more subjects has been known, which may include the electro-magnetic fields generated by the subjects' hearts. However, the means does not provide any means of broadcasting the field from one subject and transmitting it to a remote subject.

An apparatus and system to measure physical, chemical and biological parameters of the body has been known. The values can be used to trigger or produce an action or signal. The signals are transmitted to a remote data storage station by wireless transmission such as electromagnetic waves, radio waves, infrared, sound and the like, or by being reported locally by audio or visual transmission. However, the action or signal is not transmitted by any means to one or several remote users.

A system and method to measure, without physical contact, a magnetic field on a subject's chest have been known. However, the system and method do not provide by any means of broadcasting or transmitting these fields to one or several remote users.

A method for processing biomagnetic fields generated by biocurrents resulting from activities of human brain or myocardium has been known. However, the method does not provide by any means of broadcasting or transmitting these information to one or several remote users.

A biomagnetic field measuring apparatus has been known. However, the apparatus does not provide by any means of broadcasting or transmitting these information to one or several remote users.

An apparatus and a method to detect bio-signal, amplify, filter and convert bio-signal to digital bio-signal and transmit digital bio-signal have been known. However, the apparatus and method do not provide by any means broadcasting or transmitting these information to one or several remote users.

A real-time acquisition and archiving system for multiple time-sampled signals has been known. However, the system does not provide by any means broadcasting or transmitting these information to one or several remote users.

A technical system for a biomagnetometer has been known. However, the system does not provide by any means broadcasting or transmitting these information to one or several remote users.

A superconducting quantum interference device (SQUID) measurement apparatus for detecting weak magnetic field signals has been known. However, the device does not provide by any means broadcasting or transmitting these information to one or several remote users.

A portable health monitoring system having an electromagnetic field (EMF) sensor built in with the goal to promote health and prevent a disease has been known. The plurality of sensors measures the geomagnetic field, the heart rate variability (HRV), and the body temperature of a given user. This information is then transmitted to a microprocessor which is able to use this date to compute several numeric indexes which indicate the user's level of health. The invention also described how this information can be displayed so that it can be used by the given user. However, the system does not provide by any means broadcasting or transmitting these actual field from one user to another that is remote.

The complexity and progress over time to imaging the heart's magnetic field (biomagnetometry) have been described in the prior art. However, the prior art references do not provide by any means of broadcasting or applying the information to one or several users.

SUMMARY OF THE INVENTION

The present invention recognizes a system and method that can monitor, detect and/or record a biomedical-based electromagnetic field emitted by a human subject/user and communicate and/or apply the biomedical-based electromagnetic field to a remote receiver.

Accordingly, one aspect of the present invention is directed to a method of monitoring, detecting and/or recording a bio-medical-based electromagnetic field, preferably, heart rate variability (HRV) field, emitted from a first human user (also referred to as a sender), associating the electromagnetic field with a message sent by the sender and communicating and/or apply the associated message to a remote second human user (also referred to as a "receiver" or "receiving user"), by measuring and/or recording the biomedical-based electromagnetic field emitted from the sender, e.g., while the sender is communicating a message to a remote receiver, creating an electronic signal corresponding to the biomedical-based electromagnetic field and transmitting, broadcasting and/or applying the signal to the remote receiver. Preferably, the transmission or broadcasting is encoded including, but not limited to, a digital signature, and global positioning system (GPS) location data and/or the scene information.

In another aspect, the present invention contemplates additional step(s) of analyzing the received HRV field at a receiver's end (e.g., to determine the physical/emotional state of the sender) and/or transmitting and apply the received field to one or more additional receiving users, preferably, one or more additional receiving users who are participants in a collaborative online environment (e.g., a chat room or eMeeting).

According to the present invention, the received field by one or more receiving users can include the combination of the fields received from two or more users (e.g., the resulting field transmitted to the receiving user is the combination of the fields received from the two or more other users participating in a telephone conference or online chat room).

In still another aspect, after analyzing the received field, the present invention also contemplates additional steps of receiving a communication (e.g., a panic request) along with the field, analyzing the communication (e.g., to determine whether a life threatening situation exists) and comparing the communication with the analysis of the field (e.g., determining that even though the request is life threatening, the received field does not indicate any stress).

In still yet another aspect, after analyzing the received field, the present invention contemplates the additional step of generating an alert based on the analysis (e.g., sending out an alert to the lifeguards at a pool if a given user's field indicates high distress). Preferably, the alert includes, but is not limited to, the user's location (e.g., location coordinates as determined by the GPS data included in the field broadcast).

In a preferred aspect, the method of the present invention only broadcast under particular conditions (e.g., if the user's emitted electro-magnetic field passes certain threshold values).

The method of the present invention contemplates using devices for broadcasting or receiving the broadcasted signals/data corresponding to biomedical-based electromagnetic field emitted by a human user, which devices include but are not limited to, a portable device, a fixed device, a fixed phone, a mobile phone, a computer (e.g., laptop), and a personal digital assistant (PDA) (e.g., a PDA having the brand name Blackberry®).

In a further aspect, the present invention is directed to a method for transmitting and/or applying heart rate variability (HRV) data to influence the receiver's physical and emotional state. For example, the present invention contemplates a method for transmitting and/or applying a positive HRV to improve the receiver's state, which is in a life threatening situation.

DETAILED DESCRIPTION OF THE INVENTION

Figure 1:
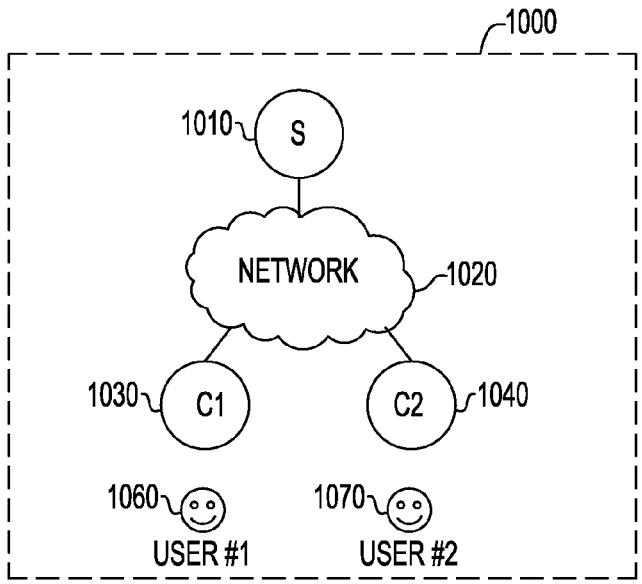
FIG. 1 is an overview an example of the Say-It-With-Feeling Service (SIWFS) network topology of one embodiment of the present disclosure.

The present invention is directed to a system and method that can monitor, detect, record, communicate and/or applying a biomedical-based electromagnetic field emitted by a human user (also referred to as a broadcaster or sender) to a remote receiver.

Accordingly, one embodiment of the present invention is directed to a method of monitoring, detecting, and/or recording a biomedical-based electromagnetic field emitted by of a first human user (also referred to as a "sender") and communicating and or applying the field to a second remote human receiver by measuring the biomedical-based electromagnetic field emitted from the sender, creating an electronic signal corresponding to the biomedical-based electromagnetic field and transmitting or broadcasting and/or applying the signal to a receiver.

By "apply" is meant to transform or put into effect the communicated, transmitted or broadcasted electronic signal corresponding to a biomedical-based electromagnetic field emitted from a human subject/user so that the receiver of the signal can be aware of, experience or feel the effect of the field. For example, the signal corresponding to a sender's HRV field can be applied to a receiver by receiving the signal by a device from the sender, assessing the HRV, e.g., by a computer equipped with a HRV analyzing software available in the art, transforming the received signal to an effect that can be felt, experienced or sensed by a human receiver and emitting, irradiating or sending out the effect to the receiver so that the receiver can feel or experience the effect of the HRV field that corresponds to the sender's mood and/or physical status. The means or device for receiving and transforming the signal and emitting the transformed effect can be a device described herein or any other device known in the art for these purposes. For example, a device that is able to receive and transform such signals is described in detail with references to FIGS. 15a and 15b; a device that is able to emit a transformed signal is described in detail with reference to FIG. 16.

In a particular embodiment, the present invention is directed to a method of monitoring, detecting and/recording a biomedical-based electromagnetic field, preferably, heart rate variability (HRV) field, emitted from a human user (also refereed to as a sender), associating the electromagnetic field with a message sent by the sender and communicating the associated message to a remote receiver, by measuring the biomedical-based electromagnetic field emitted from the sender, e.g., while the sender is communicating a message to a remote receiver, creating an electronic signal corresponding to the biomedical-based electromagnetic field (e.g., an encoded version of biomedical-based electromagnetic field) and transmitting or broadcasting and/or applying the signal to the remote receiver.

Preferably, the transmission or broadcasting is an encoded digital description of the biomedical-based electromagnetic field. To ensure validity, this encoded signal could be digitally signed, e.g., using an MD5 digital signature. In addition, this encoded digital signal can also contain addition information, including, but not limited to, a digital signature, and global positioning system (GPS) location data and/or the scene information. For example, the encoded, biomedical-based electromagnetic field signal can have additional information appended to it, this data including, but not limited to, location data (e.g., latitude and longitude) and/or scene information (e.g., indication that the sending user or sender is working from home).

In another embodiment, the present invention contemplates additional step(s) of analyzing the received field (e.g., to determine the physical/emotional state of the user) and/or applying the received field to one or more receiving users, preferably, one more users who are participants in a collaborative online environment (e.g., a chat room or eMeeting).

According to the present invention, the received field may include the combination of the fields received from two or more users (e.g., the resulting field applied to the receiving user is the combination of the fields received from the two or more other users participating in a telephone conference or online chat room).

In still another embodiment, after analyzing the received field, the present invention also contemplates additional steps of receiving a message communication (e.g., a panic request) along with the field, analyzing the message communication (e.g., to determine that it is life threatening situation) and comparing the communication with the analysis of the field to determine the authenticity of the message (e.g., determining that even though the request is life threatening, the received field does not indicate any stress).

In still yet another embodiment, after analyzing the received field, the present invention contemplates the additional step of generating an alert based on the analysis (e.g., sending out an alert to the lifeguards at a pool if a given user's field indicates high distress). Preferably, the alert includes, but is not limited to, the user's location (e.g., as determined by the GPS data included in the field broadcast).

In a preferred embodiment, the method of the present invention only broadcast under particular conditions (e.g., if the user's field passes certain threshold values).

The method of the present invention contemplates using devices from which the field is broadcast. The contemplated devices include, but are not limited to, a portable device, a fixed device, a fixed phone, a mobile phone, a computer (e.g., laptop), and a personal digital assistant (PDA) (e.g., a PDA having the brand name Blackberry®).

In a further embodiment, the present invention is directed to a method for transmitting heart rate variability (HRV) data to influence the receiver's physical and emotional state. For example, the present invention contemplates a method for transmitting a positive HRV to improve the receiver's state if they are in a life-threatening situation.

In particular, the present invention contemplates a given user to perform the following three acts:

1. A first user (sender) authorizes a message, sends it to a second user (receiver) and then has his/her (sender's) HRV field, which was recorded when the message was authored, broadcasted to the second user while the second user reads the message;
2. The first user records his/her HRV field at a particular time, and associates this HRV field with a particular symbol that can be displayed at the receiving device (e.g. an emoticon, such as ☺), and then later including this symbol in a message he/she sends to a second user (receiver), with the associated field being broadcasted to the second user while the second user reads the message containing the symbol; and
3. The first and second users participating in an online discussion (an "online room") and broadcasting their pre-recorded HRV fields to each other.

FIG. 1 shows an example of a network topology 1000 that supports the current invention. As depicted, there are two client nodes 1030 and 1040 from which user #1 1060 and user #2 1070 are able to communicate to each other via a network 1020 using server node 1010. Server 1010 will be described in detail with reference to FIGS. 2-6, and the clients nodes 1030 and 1040 will be described in detail with reference to FIGS. 7-13. One skilled in the art will appreciate that although only two client nodes (1030 and 1040) are shown in FIG. 1, the present invention contemplates any number of such client nodes. The network 1020 includes, but is not limited to, the Internet, an internal intranet, or a wireless on wired telecommunication network.

Figure 2:
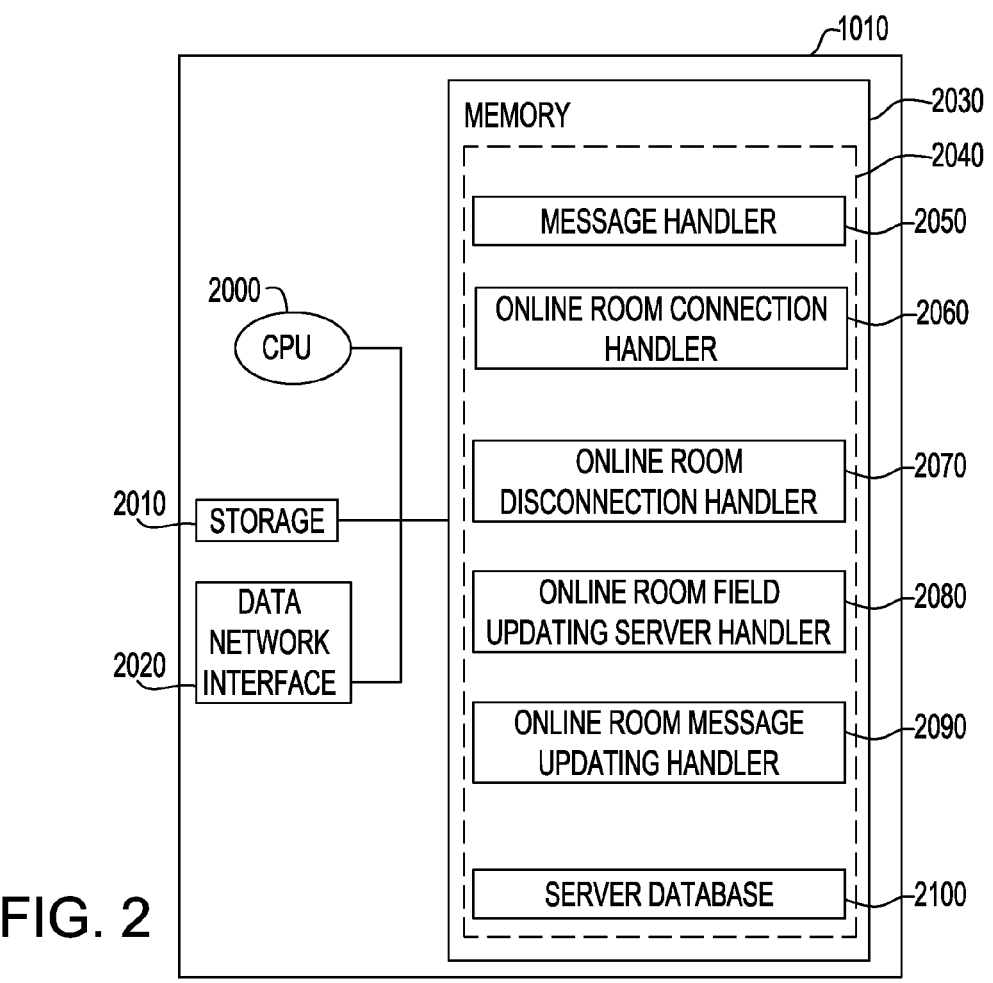
FIG. 2 is an illustrative component block diagram showing an example of a SIWFS server in one embodiment of the present disclosure.

FIG. 2 shows a block diagram of a Say-It-With-Feeling Service (SIWFS) server 1010 in one embodiment of the present invention. This system 1010 may include any computing node that is able to load and execute programmatic code, including, but not limited to: products sold by IBM such as ThinkPad® or PowerPC®, running the operating system and server application suite sold by Microsoft, e.g., Windows® XP, or a Linux operating system. The system logic 2040 is preferably embodied as computer executable code that is loaded from a remote source (e.g., from a network file system), local permanent optical (CD-ROM), magnetic storage (such as disk), or storage 2010 into memory 2030 for execution by CPU 2000. The SIWFS server 1010 also includes a data network interface card 2020, through which the SIWFS server 1010 can communicate. Such an interface 2020 may include, but is not limited to, a hardwired one, e.g., Ethernet over coax cable, wireless IP, and telephone to IP (VoIP), such as that provided by the DVG-14025 Broadband Phone Service VoIP Router from D-Link®. As will be discussed in greater detail below, the memory 2030 preferably includes computer readable instructions, data structures, program modules and application interfaces forming the following components:

a message handler 2050,
an online room connection handler 2060, described in detail with reference to FIG. 4,
an online room disconnection handler 2070,
an online room field updating server handler 2080, described in detail with reference to FIG. 6,
an online room message updating server handler 2090, and
a server database 2100.

The message handler 2050 is responsible for relaying a given message to any and all specified recipients. One with regular skill in the art will appreciate that an Instant Messaging server—like that supplied AOL's Instant Messaging—is an instance of a synchronous version of such a handler 2050. An Instant Messaging service is synchronous in the sense that a message is delivered as quickly as possible to the recipient, failing if the recipient is not available. An alternative asynchronous existing implementation of the messaging handler 2050 is an SMTP (email) Mail relay server. With SMTP, the handler 2050 would hold any sent documents until the specified recipient requested their new mail. At that point, the handler 2050 would send the message to the requesting node's email client. This handler is discussed further with reference to FIGS. 9, 10 and 11. What both Instant Messaging and email services lack is the ability of the reader/receiver of a given message or note to have the HRV field of the sender broadcast to the reader/receiver when the reader/receiver reads the given message or note.

The online room disconnection handler 2070 in one embodiment of the present disclosure enables a given user to leave (quit) a given online room in which they are already participating. When a disconnection request from a given user (e.g., 1060) for a given room (e.g., an outdoor sports discussion room) is received, the handler 2070 modifies the entry in the server database 2100 for the given room, deleting the given user from the list of participants. This means deletion will terminate the forwarding of all of the given room's field and message updates from the online room field updating server handler 2080 and online room message updating handler 2090.

The memory 2030 also contains an online room message updating server handler 2090, which supports an online discussion forum, henceforth referred to as an "online room." The online room service allows users to join and participate one of several available online rooms—this activity usually being the posting of related messages. In the SIWFS server 1010, the list of all of the available rooms and each of the room's current members is stored in the server database 2100. Existing examples of such a services include chat rooms, like that supplied by both Sametime Meeting and the Easy Chat Server. What both of these services lack is for a given participant to have the HRV fields of all of the other room members broadcast to him/her while he/she participates. The room message updating server handler 2090 is responsible for forwarding any posting from one user to all of the other room members. To accomplish this, whenever a online room message is received, the handler 2090:

determines the message's room (specified in the message),
determines all of the given room's participants from the server database 2100, and then
sends the new message to all of the participants.

This handler 2090 will be discussed further with reference to FIGS. 12 and 13.

The memory 2030 also includes the server database 2100, in one embodiment, which provides for the creation, deletion and modification of persistent data (such as the users' names, their ID's, the chat rooms and their active member lists, and extended emoticon definitions), and is used by the handlers 2050-2090 of the SIWFS server 1010. An example of a product providing such function includes IBM DB/2 database system.

Figure 3:
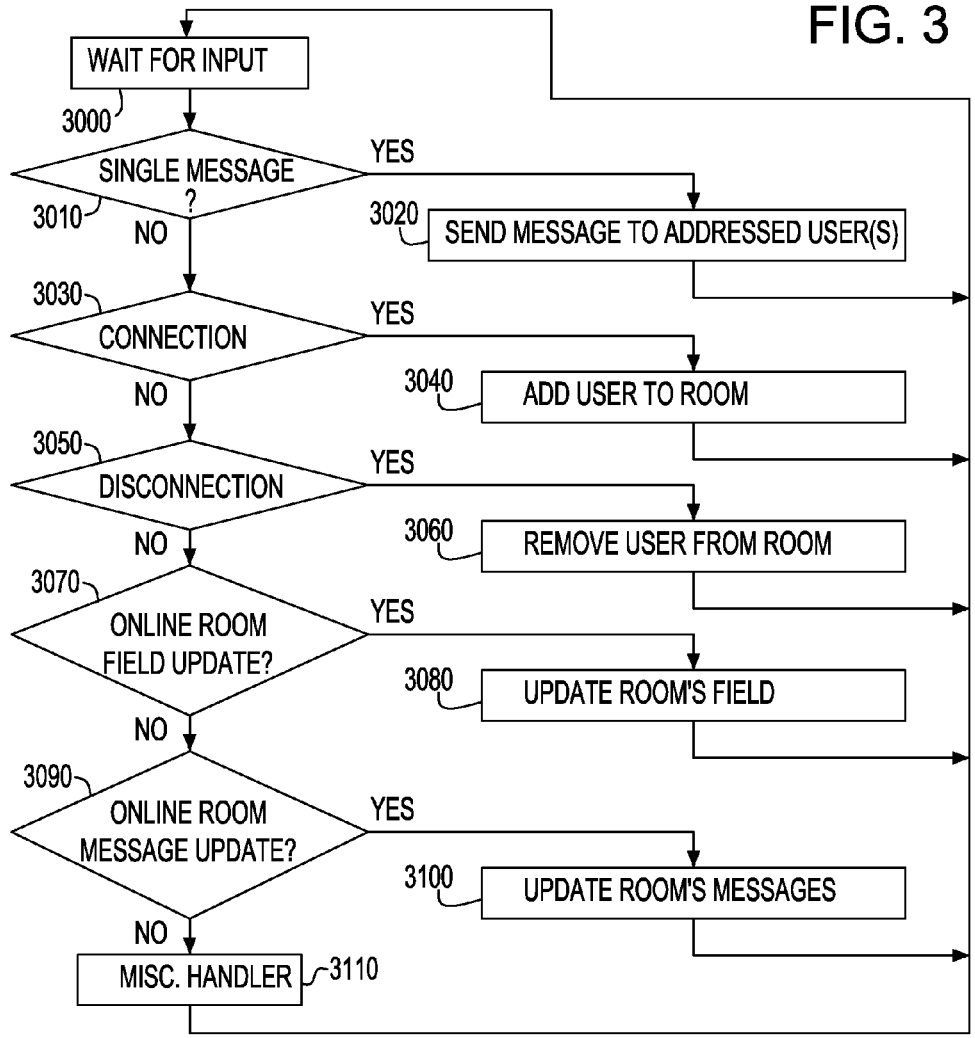
FIG. 3 is a flow diagram illustrating the flow control of an SIWFS server in one embodiment of the present disclosure.

FIG. 3 is a flow diagram illustrating the control flow of the SIWFS server's logic 2040 in one embodiment of the present invention. At step 3000, the server 1010 waits for message or online chat request inputs. When such an input is received, step 3010 checks whether it is a message-sending request from a client node 1030/1040 (FIG. 1). If so, then the message handler 2050 is invoked in step 3020, to process the request, following which control continues at step 3000. If the input is not a message-sending request, then step 3030 checks whether it is a request by a user to join an online room. If so, the online room connection handler 2060 is invoked in step 3040, following which control continues at step 3000. If the input is not an online room connection request, then step 3050 checks whether it is a request by a user to leave an online room. If so, the online room disconnection handler 2070 is invoked in step 3060, following which control continues at step 3000. If the input is not an online room disconnection request, then step 3070 checks whether it is an online room field update request. If so, the online room field updating server handler 2080 is invoked in step 3080, following which control continues at step 3000. If the input is not an online room field updating request, then step 3090 checks whether it is an online room message update request. If so, the online room message updating handler 2090 is invoked in step 3100, following which control continues at step 3000. If the input is not an online room message update, then a miscellaneous handler beyond the scope of the current invention is invoked in step 3110, following which control continues at step 3000.

Figure 4:
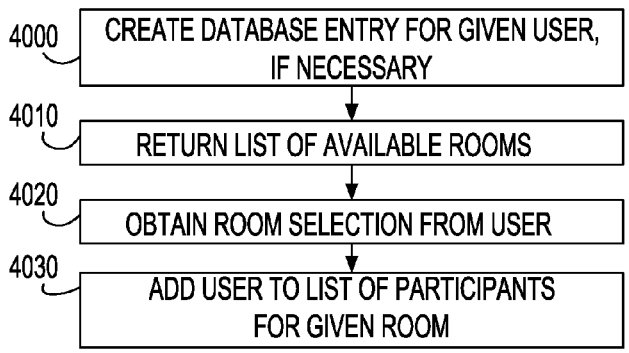
FIG. 4 is a flow diagram illustrating the flow control of the online room connection handler in one embodiment of the present disclosure.

FIG. 4 is a flow diagram illustrating the control flow of the online room connection handler 2060 in one embodiment of the present invention, which is responsible for processing a request from a given user (e.g., 1060) join and participate in a specified online room. As shown in step 4000, the handler 2060 first checks the server database 2100, creating a new entry for the requesting user if they do not already have an entry. In step 4010, the handler 2060 returns a list of all available online rooms to the requesting user's node 1030, obtaining the user's selection is step 4020. The handler 2060 then adds the given user to the specified online room in step 4030 recording this fact in the server database 2100.

Figure 5:
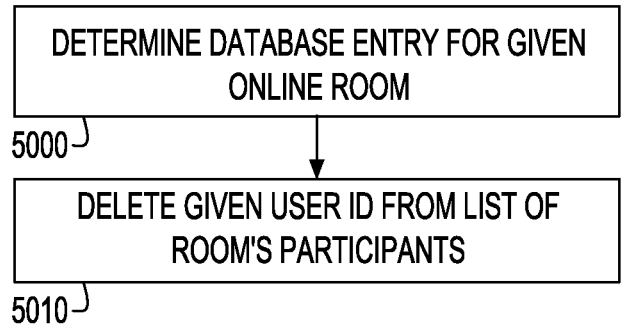
FIG. 5 illustrates an online room disconnection handler logic.

FIG. 5 is a flow diagram illustrating the control flow of the online room disconnection handler 2070 in one embodiment of the present disclosure, which enables a given user to leave (quit) a given online room in which they are already participating. When invoked, the handler 2070 is passed both the ID of the relevant user (e.g., 1060) and online room (e.g., the outdoor sports discussion room). As shown, in step 5000, the handler 2070 first finds the entry for the given room in the server database 2100. Then in steps 5010, the handler 2070 modifies the entry in the server database 2100, deleting the given user from the list of participants. This means deletion will terminate the forwarding of all of the given room's field and message updates from the online room field updating server handler 2080 and online room message updating handler 2090.

Figure 6:
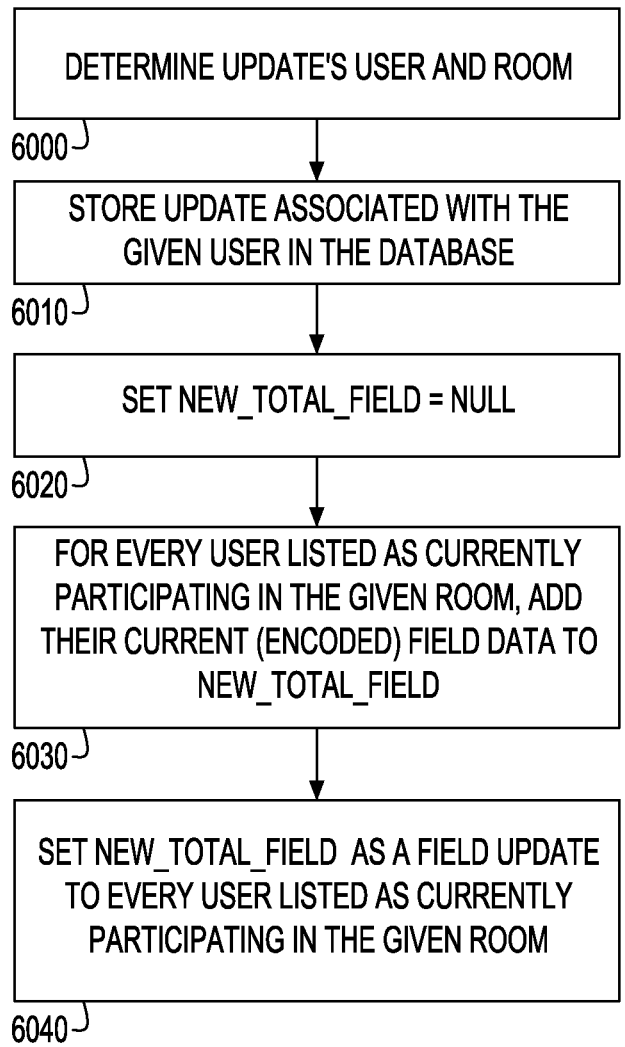
FIG. 6 is a flow diagram illustrating the flow control of the online room field updating server handler in one embodiment of the present disclosure.

FIG. 6 is a flow diagram illustrating the control flow of the online room field updating server handler 2080 in one embodiment of the present invention. This handler 2080 is responsible for calculating and sending each of a given room's participants the updated combined field of all of the room's current participants. This handler 2080 uses field updates sent by each user—from their node's online room field updating client handler 7140—the information in these updates including, but not limited to, the following:
- the user's ID,
- the user's node,
- the online room,
- the user's location in the room,
- the user's direction (of gaze) in the room,
- an encoding of the user's field.

As shown in FIG. 6, in step 6000 the handler 2080 first determines the given update's user and online room, storing the update in server database 2100, and associating it with the given user in step 6010. Next, in step 6020, the handler's 2080 NEW_TOTAL_FIELD variable is set to null (zero). Then, in step 6030, the handler 2080 sums together the fields of every user currently participating in the online room, storing the sum in NEW_TOTAL_FIELD. In step 6040, the handler 2080 sends this updated online room field to each of the given online participants (specifically to the online room field updating client handler 7140 running on each participating users node 7000).

Figure 7:
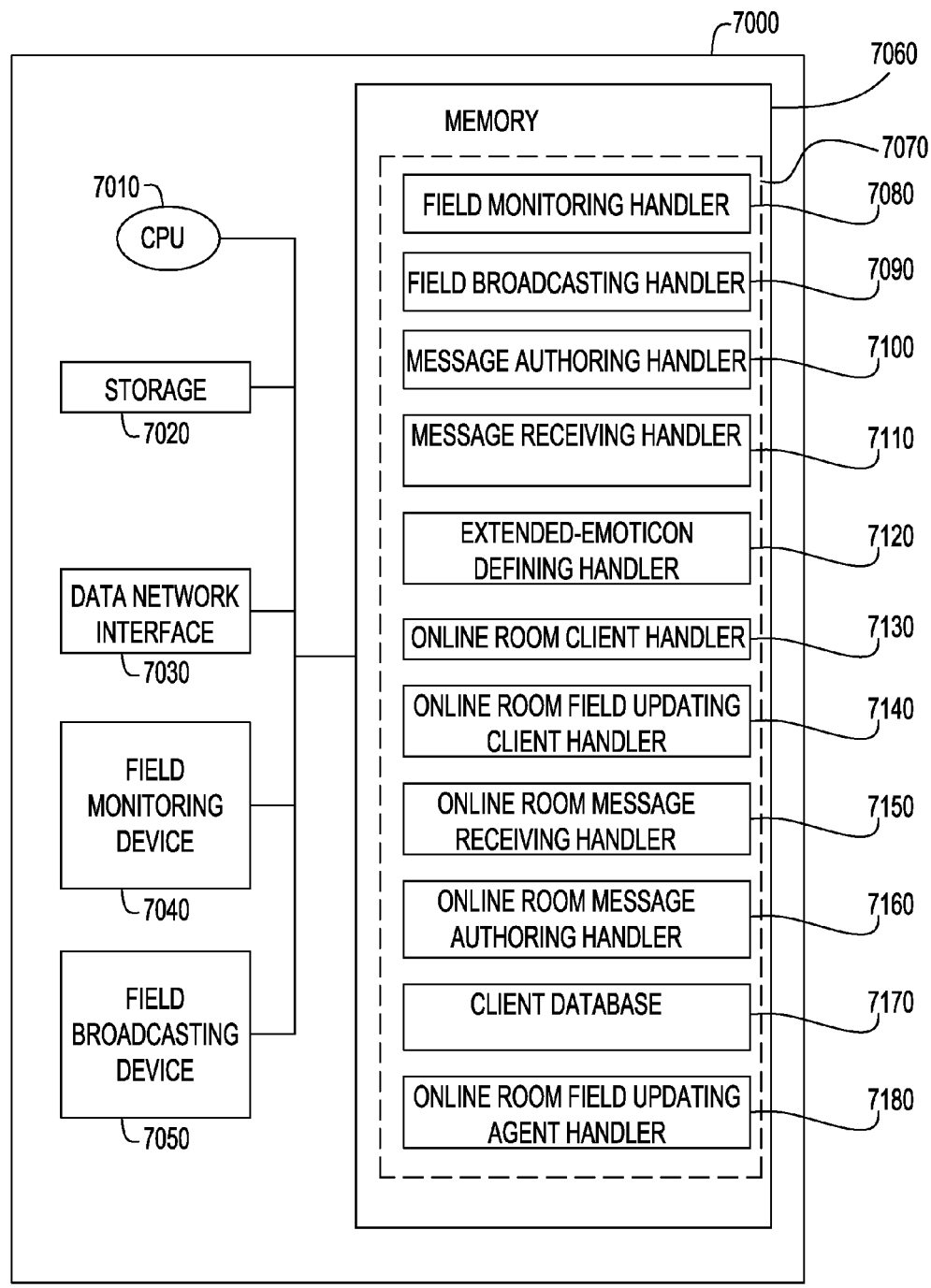
FIG. 7 is an illustrative component block diagram showing an example of a SIWFS client in one embodiment of the present disclosure.

FIG. 7 depicts a more detailed component diagram of a SIWFS client node 7000 in one embodiment of the current invention, which represents the client nodes 1030 and 1040 of FIG. 1. Such a client 7000 may comprise any computing node that is able to load and execute programmatic code and communicate via a network, including, but not limited to: an IBM ThinkPad running Windows XP. Additional platforms include network-connectable mobile (i.e., portable) devices such as those sold under the trademark Blackberry by RIM, as well as smart cellular telephones (i.e., devices which can act as a cellular telephone as well as run network applications), e.g., Nokia 90008 by Nokia. As shown in FIG. 7, client 7000 preferably includes:
- a processor device, CPU 7010,
- a storage device 7020 such as a magnetic or optical disk storage or a direct access storage device (DASD),
- a network interface 7030,
- a field monitoring device 7040, described in detail with reference to FIG. 15a,
- a field broadcasting device 7050, described in detail with reference to FIG. 16, and
- a memory 7060, such as RAM.

According to the present invention, the client logic 7070 is preferably embodied as computer executable code that is loaded from a remote source (e.g., over the network 1020 via the network interface 7030), local permanent optical (CD-ROM), magnetic storage (such as disk), or DASD 7020 into memory 7070 for execution by CPU 7010. As will be discussed in greater detail herein below, the memory 7070 preferably includes computer readable instructions, data structures, program modules and application interfaces forming the following components:
- a field monitoring handler 7080, described in detail with reference to FIG. 15b;
- a field broadcasting handler 7090, described in detail with reference to FIG. 16;
- a message authoring handler 7100, described in detail with reference to FIG. 9;
- a message receiving handler 7110, described in detail with reference to FIG. 10;
- an extended-emoticon defining handler 7120, described in detail with reference to FIG. 11;
- an online room client handler 7130, described in detail with reference to FIG. 12;
- an online room field updating client handler 7140, described in detail with reference to FIG. 13;
- an online room message receiving handler 7150,
- an online room message authoring handler 7160,
- a client database 7170, and a
- an online room field updating agent handler 7180, described in detail with reference to FIG. 14.

Figure 15A:
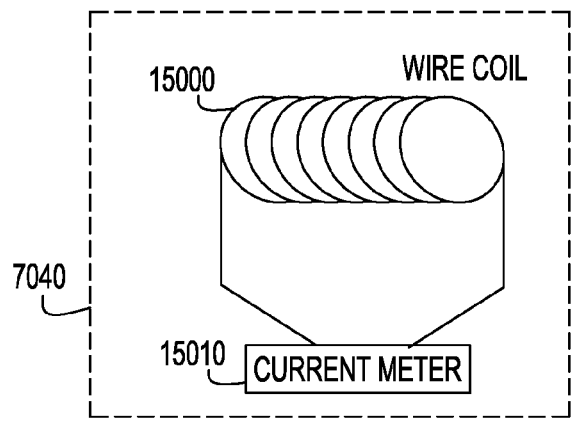
FIG. 15a is an illustrative component block diagram showing an example of a field monitoring device in one embodiment of the present disclosure.

FIG. 15a depicts the field monitoring device 7040 in one embodiment of the current invention. As shown, there is a wire coil 15000 attached to a computer accessible current meter 15010 (e.g., accessible via an RS232 connection). Whenever the heart of the user of the node 7000 user generates a magnetic field, this field induces a current in coil 15000 which can be measured by the current meter 15010, which in turn, can be retrieved by the field monitoring handler 7080 (e.g., via the RS232 connection).

Figure 15B:
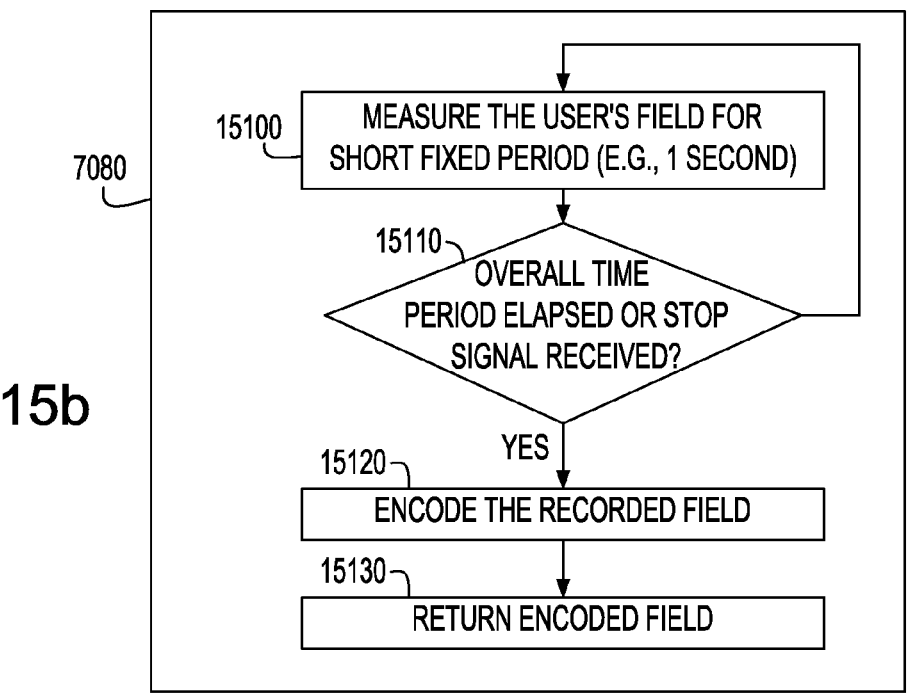
FIG. 15b is a flow diagram illustrating the flow control of the field monitoring handler in one embodiment of the present disclosure.

FIG. 15b depicts a flow diagram illustrating the control flow of the field monitoring handler 7080, which is responsible for measuring and recording the HRV field of the node 7000 user, and then returning a digital encoding of it. As shown, in step 15100, the handler 7080 retrieves the current measured by the current meter 15010 of the field monitoring device 7040 for a fixed period of sampling time (e.g. $\frac{1}{100}$ of a second, this value possibly passed to the handler 7080 when the field reading is requested). Next, in step 15110, the handler 7080 checks whether the overall reading is complete. This consists of either checking that a specified overall time period had elapsed (e.g. 30 seconds) or that a stop signal has been received (e.g., a computer interrupt signal from one of hander 7100-7160). If not, control continues at step 15100. Otherwise, in step 15120, the handle 7080 encodes the readings that is has taken for the current request. In one embodiment of the current invention, the digital encoding of the given measurement returned by the field monitoring handler 7080 consists of an indication of how long each sampling lasted (e.g., $\frac{1}{100}$ of a second) followed by a list of each of the readings (i.e. a decimal indicating the current retrieved from the current meter 15100). So, for example, if a given user's HRV field was read for 30 seconds with a $\frac{1}{100}$ of a second sampling length, the returned encoding of their HRV field would consist of the fraction "$\frac{1}{100}$" followed by a list of 3000 values, each one indicating the current measured by the current meter 15010 during a sampling period. One with regular skill in the art will appreciate that encodings using lengths of time other than $\frac{1}{100}$ second (e.g., $\frac{1}{1000}$ of a second) are also within the scope of the current invention. Further, rather than just a single recording, the field monitoring handler 7080 could use the average (or some other combination) of the readings taken during the given sampling time interval.

Figure 16:
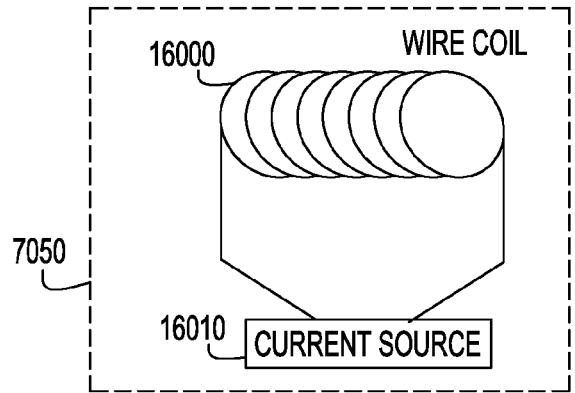
FIG. 16 is an illustrative component block diagram showing an example of a field broadcasting device in one embodiment of the present disclosure.

The field broadcasting handler 7090 is responsible for decoding a received encoding of an HRV field and then broadcasting this field to the node user (1060 or 1070). So, if user 1060 sent a message to user 1070, this handler 7090 would provide user 1070 with user 1060's HRV by first decoding what it is passed and then applying (radiating) user 1070. To broadcast the actual the signal, the field broadcasting handler 7090 employs the field broadcasting device 7050, a more detailed component block of one embodiment of which is depicted in FIG. 16. As shown, there is a wire coil 16000 which is connected to a computer controllable current source 16010. When current is driven through the coil 16000, a magnetic field is induced, which will radiate the user of the given node 7000. In one embodiment of the current invention (as described above with reference to FIG. 15b), the encoding of the HRV field consists of a first number representing the length of each sampling period followed by a list of numbers, each number representing the level of current to generate (i.e., with the current source 16010) for each sampling period. Thus, to broadcast a given signal, the field broadcasting handler 7090, first sets the sampling period using the first number from a given encoding. The field broadcasting handler 7090 then reads each following number from the encoded HRV field and commands the current source 16010 to generate that level for the specified sampling period. When all of the numbers have been read from the encoding, the current source 16010 is set down to 0.

The online room message receiving handler 7150 is responsible to displaying messages related to a specified online room. Examples of such handlers include those sold by IBM under the trademark Sametime® Meeting. This handler enables the display of a received message linking to the specified online room and indicating the message's sender. E.g., if a user with ID "Ron" sends the message, "Me too," to the Co-workers online room in which the node user is participating, the handler 7150 could provide a window which includes:

Ron: Me too in a window being labeled "Coworkers" and containing previously received messages.

The online room message authoring handler 7160 is responsible for enabling the node user to author and send her own messages to a given online room. IBM's Sametime meeting provides such an authoring GUI. This GUI allows user to select rooms and then author comments that are sent to the given room.

The client database 7170, in one embodiment of the current invention, provides for the creation, deletion and modification of persistent data, and is used by the handlers 7080-7160 and 7180 of the SIWFS client 7000. An example of a product providing such function includes the IBM DB/2 database system.

Figure 8:
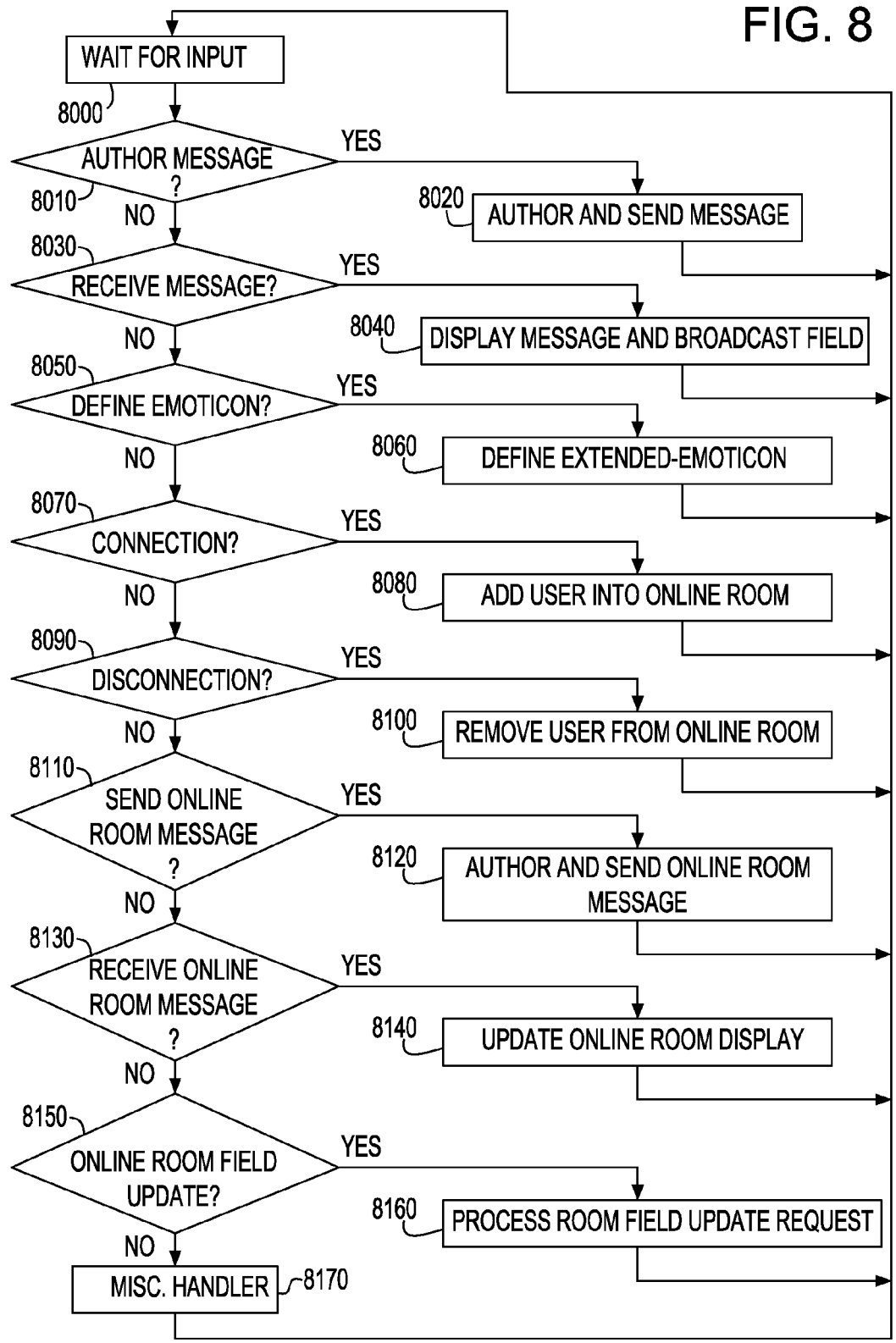
FIG. 8 is a flow diagram illustrating the flow control of an SIWFS client in one embodiment of the present disclosure.

FIG. 8 is a flow diagram illustrating the control flow of the SIWFS client's logic 7070 in one embodiment of the present disclosure. At step 8000, the client 7000 waits for input. When an input is received, step 8010 determines whether it is a message authoring request. If so, the message authoring handler 7100 is invoked in step 8020, following which control continues at step 8000. If the input is not a message authoring request, then step 8030 checks whether it is a request to receive a message. If so, the message receiving handler 7110 is invoked in step 8040, following which control continues at step 8000. If the input is not a message receiving request, then step 8050 checks whether it is a request to define an extended-emoticon. If so, the extended-emoticon defining handler 7120 is invoked in step 8060, following which control continues at step 8000. If the input is not an extended-emoticon defining request, then step 8070 checks whether it is a request to connect to an online room. If so, the online room client handler 7130 is invoked in step 8080, following which control continues at step 8000. Otherwise, step 8090 checks whether it is a request to disconnect from an online room. If so, the online room client handler 7130 is invoked in step 8100, following which control continues at step 8000. If the input is not an online room disconnection request, then step 8110 checks whether it is a request to send a message to an online room. If so, the online room message authoring handler 7160 is invoked in step 8120, following which control continues at step 8000. If the input is not an online room message sending request, then step 8130 checks whether it is a request to process an incoming online room message. If so, the online room message receiving handler 7150 is invoked in step 8140, following which control continues at step 8000. If the input is not an online room message receiving request, then step 8150 checks whether the input is an online room field update related request. If so, the online room field updating client handler 7140 in step 8160, following which control continues at step 8000. If the input is not an online room field update related request, then a miscellaneous handler beyond the scope of the current invention is invoked in step 8150, following which control continues at step 8000.

Figure 9:
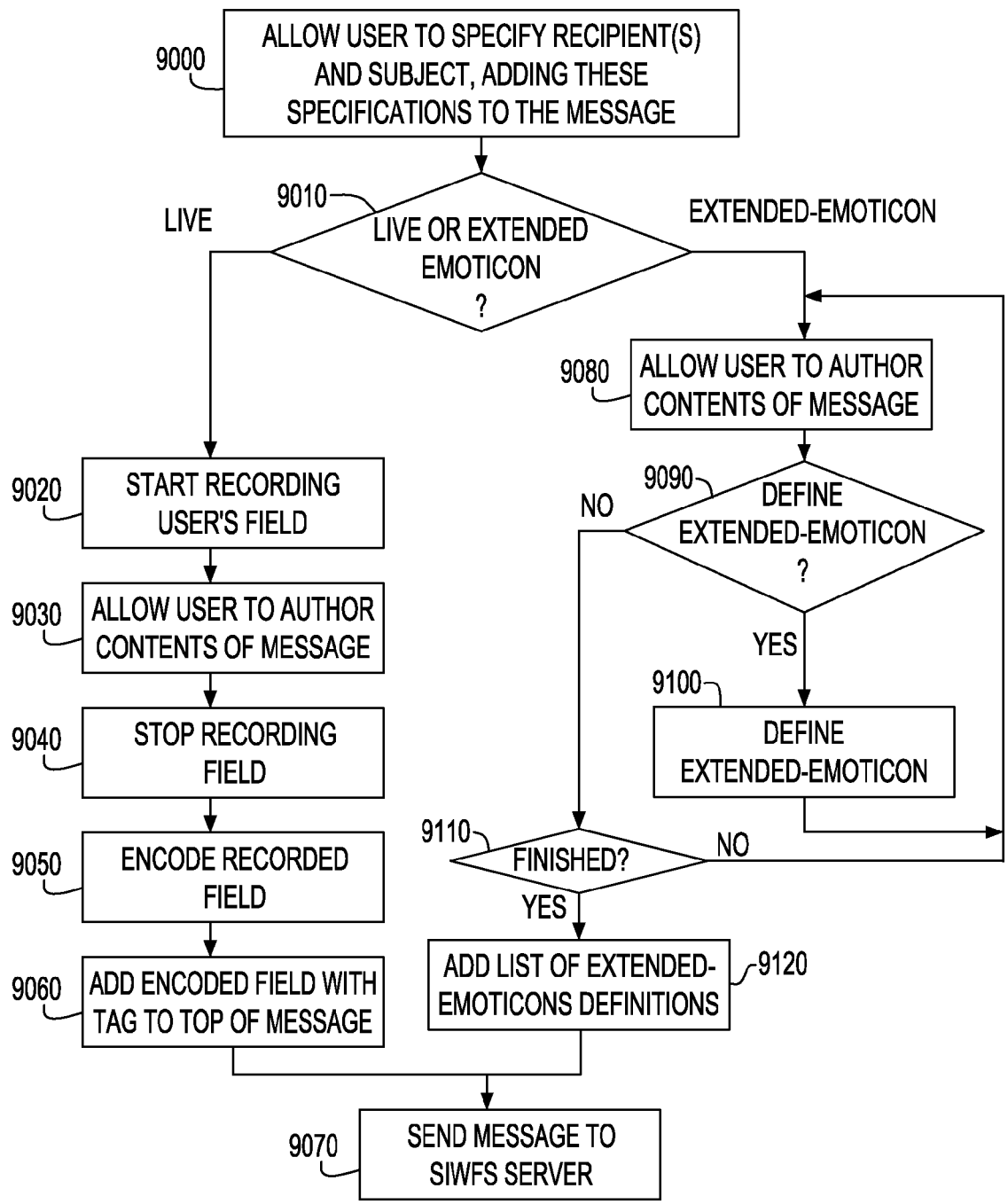
FIG. 9 is a flow diagram illustrating the flow control of the message authoring handler in one embodiment of the present disclosure.

FIG. 9 is a flow diagram illustrating the control flow of the message authoring handler 7100 in one embodiment of the present disclosure. This handler 7100 enables a user (e.g., 1060) to create and send a message to another user (e.g., 1070), this message containing not only context like text and graphics which can be viewed by the recipient, but also an encoding of the HRV field of the author, this encoded data being decoded and broadcast to (i.e., radiated on) the recipient when they read the message. As shown, in step 9000, the handler 7100 has the sender (e.g., 1060) specify the recipient of the message (e.g., 1070). One with regular skill in the art will appreciate that in the case where the message protocol is SMTP (email), the sender would specify the email address of the recipients. Similarly, if the message protocol is instant messaging (e.g., that provided by Lotus Sametime Instant Messaging), the sender specifies the instant messaging ID of the recipient. Step 9000 also allows the sender to specify the subject of the message if the messaging protocol is SMTP. Next, in step 9010, the handler 7100 checks whether the sender wants to send an encoding of their HRV field throughout the time they author the given note, or if they want to use extended-emoticons instead (extended emoticon also discussed further in detail with reference to FIG. 11). If the sender elects to use the encoding of her HRV field for the entire authoring session, then, in step 9020, the field monitoring handler 7080 is invoked to start recording the sender's HRV field. Next, in step 9030, the handler allows/enables the sender to specify the contents of her message (e.g., text and graphics). Once the user is finished, the handler 7100 tells the field monitoring handler 7080 to stop recording in step 9040, and return and encoding or the recorded HRV field history in step 9050. The handler 7100 then adds a tagged field to the authored message which contains the encoded HRV field history. Finally, in step 9070, the completed message is sent to the message handler 2050 running on the SIWFS server 1010.

Alternatively, if the sender has indicated that she only wants to include extended-emoticons in her message, then in step 9080 the handler 7100 allows the sender to author her message, embedding an emoticon (e.g., the ☺ or ☹ symbol) in her authorized note. In step 9090, the user is able to indicate that they wish to define an extended-emoticon. If she does, then in step 9100 the extended-emoticon defining handler 2120 is invoked, following which control continues at step 9080 where the user is allowed to continue editing her message. As will be described further with reference to FIG. 11, each extended-emoticon definition is stored in the client database 7170. Thus, a user can reuse an extended-emoticon that they have previously defined using the extended-emoticon defining handler. For example, if user 1060 previously defined an extended-emotion associated with the ☹ symbol, she could include this symbol in her message and have the previous definition used; she would not have to redefine the symbol for the current message unless she wanted to. The user can also indicate that she has completed her message in step 9110. When this occurs, the handler 7100 adds tagged fields into the message (e.g., at the top of the message) which specify the definitions of all emoticons found in the message that have an associated extended-emoticon definition. So, for example, if the message contains both the ☹ and the ☺ emoticons and there is only an extended-emoticon definition for ☹, then only the definition for ☹ will be included as a tagged field; ☺ will be left undefined. Each of these definitions includes both an encoded HRV field and the associate emoticon symbol (e.g., ☹). Finally, in step 9070, the completed message is sent to the message handler 2050 running on the SIWFS server 1010.

Figure 10:
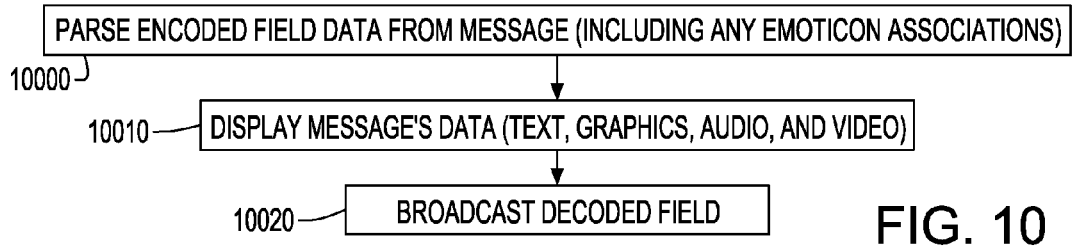
FIG. 10 is a flow diagram illustrating the flow control of the message receiving handler in one embodiment of the present disclosure.

FIG. 10 is a flow diagram illustrating the control flow of the message receiving handler 7110 in one embodiment of the present invention. This handler 7110 is responsible for displaying a sent message's contents as well as broadcasting any encoded HRV field data to the reader. In step 10000, the handler 7110 parses the entire message, extracting any encoded HRV field data from tagged fields/sections in the message. This includes the history HRV field while author created the message, or any definitions HRV fields associated emoticon symbols. In step 10010, the handler 7110 displays the contents to the viewing user (e.g., 1070) and in step 10020 broadcasts the encoded HRV field data when appropriate by passing the encoded HRV field to the field broadcasting handler 7090. So, for example, if the author included extended-emoticons, then the handler 7110 will only broadcast the associated HRV field to the reader when they reach the associated emoticons. One with regular skill in the art will appreciate that the reader could also have the HRV field related to a given emoticon broadcast to them when the selected (e.g., double-clicked) the associated emoticon.

Figure 11:
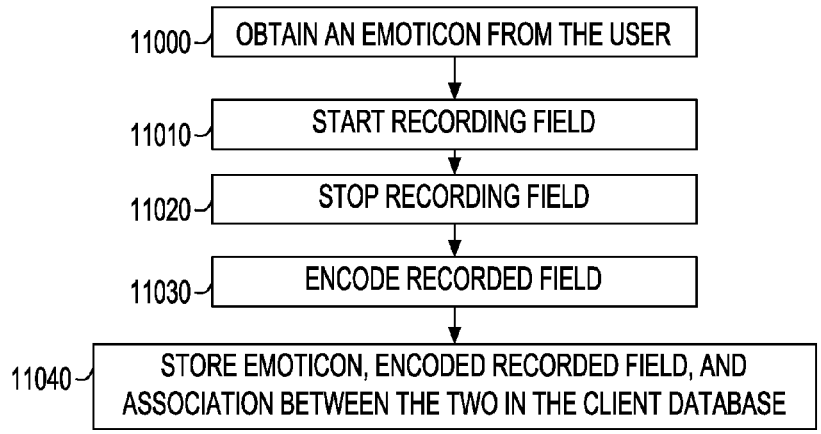
FIG. 11 is a flow diagram illustrating the flow control of the extended-emoticon defining handler in one embodiment of the present disclosure.

FIG. 11 is a flow diagram illustrating the control flow of the extended-emoticon defining handler 7120 in one embodiment of the present disclosure. This handler 7120 is responsible for allowing a given user to record and associate particular HRV fields (in encoded form) with particular symbols, e.g., emoticons, such as ☺ and ☹. In step 11000, the user specifies a particular emoticon system (e.g., ☹). Then, in step 11010 the handler 7129 invokes the field monitoring handler 7080 to start recording the user's HRV field. Next, in step 11020, after a preset period of time, or when indicated by the user, the field monitoring handler 7080 stops recording the user's HRV field, and, in step 11030 returns an encoded version of its readings. Lastly, in step 11040, the extended-emoticon defining handler 7120, stores an extended-emoticon definition in the client database 7170, this definition including the specified (emoticon) symbol, the returned encoded HRV field, and the fact that the two are associated to each other.

Figure 12:
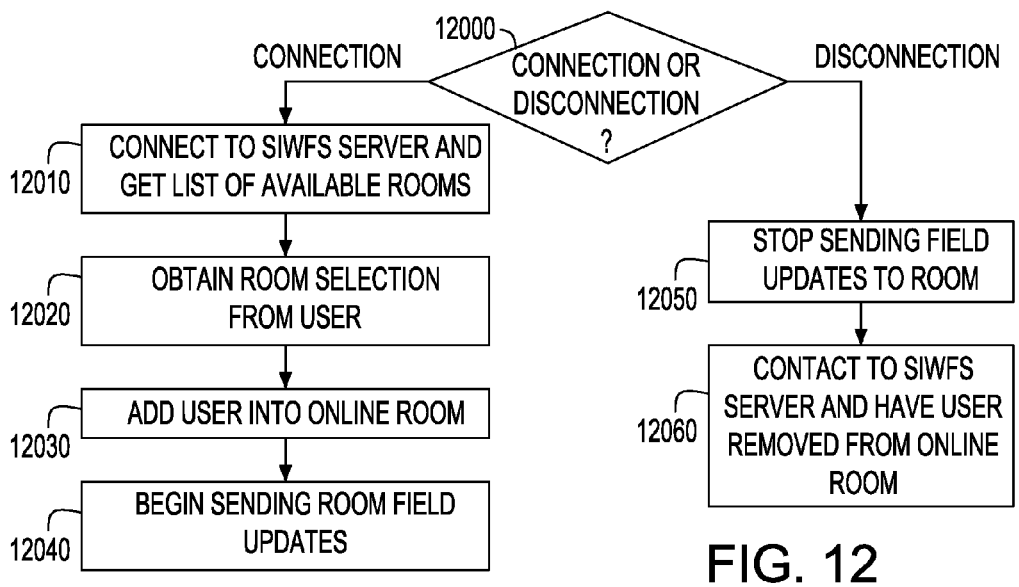
FIG. 12 is a flow diagram illustrating the flow control of the online room client handler in one embodiment of the present disclosure.

FIG. 12 is a flow diagram illustrating the control flow of the online room client handler 7130 in one embodiment of the present disclosure. This handler 7130 allows a given user to both join and leave online rooms. Step 12000 determines whether the current request is to connect or to disconnect. If it is a connection request, then in step 12010 the handler 7130 contacts the SIWFS server 1010 and retrieves the current list of available online rooms. In step 12020 the user selects one of these rooms, and in step 12030 this selection is sent to the online room connection handler 2060 running on the SIWFS server 1010, which adds the given user to the specified room. Then, in step 12040, the online room field updating client handler 7140 (described in detail with reference to FIG. 13) is invoked to begin sending updates of the user's HRV field to the SIWFS server 1010 with respect to the selected online room. Alternatively, if the request for one from the user to disconnect from a given online room, then, in step 12050, the online room field updating client handler 7140 is told to step sending HRV field updates for the user for the given online room. Lastly, in step 12060, online room disconnection handler 2070 running on the SIWFS server 1010 is contacted and told to remove the given user from the given room.

Figure 13:
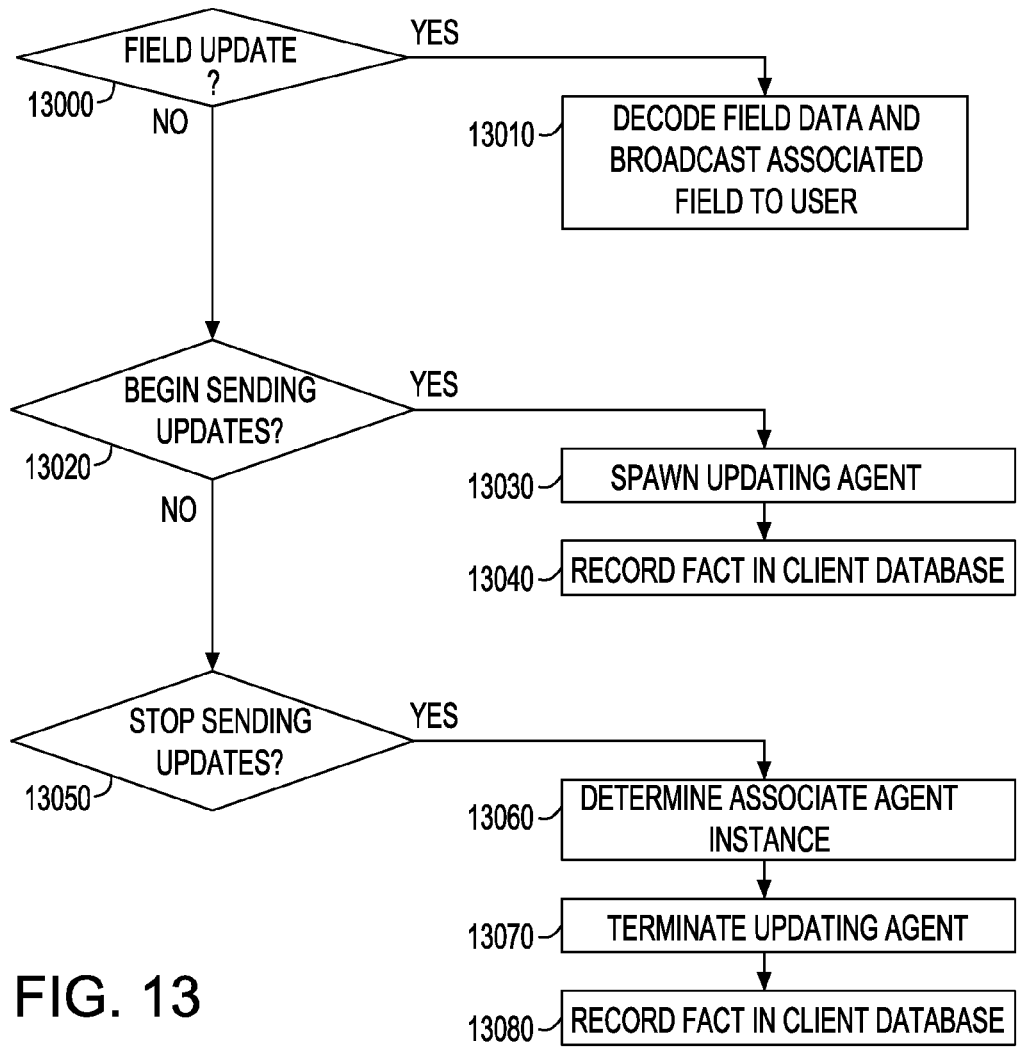
FIG. 13 is a flow diagram illustrating the flow control of the online room field updating client handler in one embodiment of the present disclosure.

FIG. 13 is a flow diagram illustrating the control flow of the online room field updating client handler 7140 in one embodiment of the present disclosure. This handler 7140 is responsible for handling all requests to the client 7000 related to updating online room field broadcasts. As shown, in step 13000 the handler 7140 first checks whether the given request is one containing new encoded field data to broadcast to the node's user. If so, in step 13010, the handler 7140 passes the encoded data to the field broadcasting handler 7090, which decodes the data and then broadcasts described field to the node user. If not, step 13020 checks whether the input is a request to begin sending updates of the node user's HRV field to a specified online room. If so, then in step 13030, the handler 7140 spawns an instance of the online room field updating agent handler 7180 (described in detail with reference to FIG. 14.) indicating the specified online room. Then, in step 13040, the handler 7140 records the fact that the node user's field is being sent to the SIWFS server 1010 for the specified room in the client database 7170, including the identification of the agent instance handling these updates. Otherwise, in step 13050, the handler 7140 checks whether the request is one stop sending field updates to a specified room. If so, the handler 7140 first queries the client database 7170 to determine which instance of the online room field updating agent handler 7180 is sending updates to the specified online room. Next, in step 13070 this instance is terminated, following which the client database 7170 is updated to indicate this in step 13080.

Figure 14:
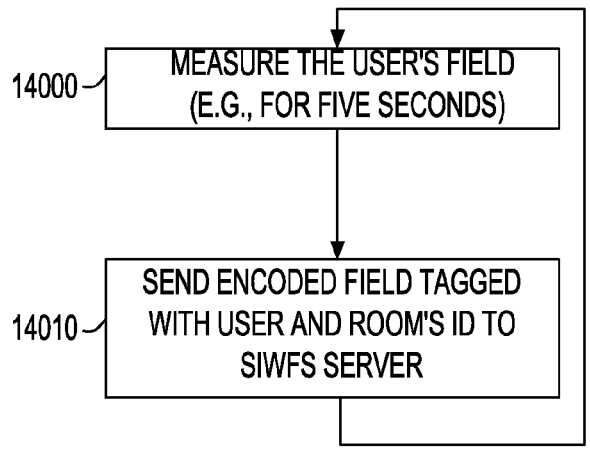
FIG. 14 is a flow diagram illustrating the flow control of the online room field updating agent handler in one embodiment of the present disclosure.

FIG. 14 is a flow diagram illustrating the control flow of the online room field updating agent handler 7180 in one embodiment of the present disclosure. This handler 7180 is responsible for periodically updating the node user's HRV field in a specified online room. Whenever the node user joins a specified online room, a new instance of the online room field updating agent handler 7180 is created and run, this instance being passed the ID's of both the node user and target online room. The instance then periodically measures, encodes and then sends updates to the online room field updating server handler 2080 running on the SIWFS server 1010 for the given room and user. The given instance runs until being terminated by the online room field updating client handler 7140. In one embodiment of the current invention, as show in FIG. 14, in step 14000 this handler 7180 first invokes the field monitoring handler 7080 to obtain an encoding of 5 seconds of the node user's HRV field. In step 14010 the handler 7180 sends this encoded data tagged with the ID of the node and the specified online room to the online room field updating server handler 2080 running on the SIWFS server 1010. Control then continue at step 14000. One with regular skill in the art will appreciate the other methods of periodically recording and sending the node user's HRV field are within the scope of the current invention, including, but not limited to recording the HRV field for a fixed time period then pausing, or analyzing the encoded HRV field and only sending updates when the recorded data changes (thus reducing network communication from the client 7000 to the server 1010).

EXAMPLES

Usage Scenarios

The following are three examples and non-limiting usage scenarios, which demonstrate features of the present invention.

Example Usage Scenario #1, in which Buddy sends a message note to his colleague Helga, demonstrates communication that includes and provides Buddy's HRV field to Helga when Helga reads the note.
1. Buddy brings up SIWFS GUI on his computer in order to send a message note to his colleague Helga, describing how happy and contented he is working on his current project.
2. Since Buddy is feeling precisely this happiness and contentment as he writes the note, he selects the record-field option when he starts authoring the note.
3. The SIWFS client begins recording his HRV field in the manner as described in the present application.
4. Once he finished authoring the note, Buddy selects the Send command.
5. The SIWFS client encodes the HRV field data that it has recorded and includes it as an attachment to the note its sends to Helga.
Helga receives the note from Buddy on her SIWFS client. When she reads the note, Helga not only is shown all of the data (e.g., text and graphics) that Buddy sent, but she also has Buddy's HRV field applied to her decoded from the data attached to Buddy's message so that she can feel the HRV field or happiness of Buddy. Note that if Helga had read Buddy's note using a standard IM client, then the encoded HRV field data would have been ignored.

Example Usage Scenario #2, in which Buddy sends a message to Helga that includes an extended-emoticon, which provides one of Buddy's particular HRV fields to Helga when she reads the note.
1. At one point using his SIWFS client, Buddy records his HRV field when he is feeling particularly sad, tagging this data with the ☹ emoticon. The SIWFS client stores this data—in encrypted form along with its association to ☹ or future use.
2. At a later time, Buddy learns that he is being reassigned a new project, which is sure to be irritating. Using the SIWFS client's message authoring application, Buddy writes another message to his colleague, Helga. In the note, Buddy explains the situation, ending the description with the ☹ emoticon.
3. When he sends the note, the SIWFS client, includes the encrypted HRV field data associated with the ☹ emoticon, as well as an indication that the ☹ emoticon should be associated with the given encrypted HRV field data.
Helga receives the note from Buddy, and begins reading its using the SIWFS message application on her computer. As soon as the ☹ emoticon becomes visible to Helga, the SIWFS message application decodes the HRV field data and applies it to her so that she can feel the HRV field or sadness of Buddy.

Example Usage Scenario #3, in which Buddy participates in an online community in which all of the other participants' HRV fields are sent and applied to all of the other participants.
1. Buddy brings up SIWFS online community application on his computer and connects to the SIWFS Server.
2. The SIWFS online community application downloads the available discussion rooms from the SIWFS server, and begins monitoring Buddy's HRV field.
3. Buddy chooses the What-Bugs-Me room. As soon as he does, the online community application begins sending an encoded form of Buddy's HRV data to SIWFS server.
4. The SIWFS online community application on Buddy's client also listens for updates from the SIWFS server. Whenever one arrives, the online community application not only displays the new data, but also decodes and applies the included encoded HRV field data to Buddy. This HRV field is the sum of the HRV fields of all of the room's current participants combined in the manner as described in greater details herein. Thus, each participant not only reads what the others are saying, but can also feel the common HRV field, just as if they were all together. Note that the online community application may receive updates from the server which contain only HRV field updates.

The present invention has been described with reference to diagrams of methods, apparatus (systems) and computer program products according to embodiments of the invention. It will be understood that each diagram, can be implemented by computer program instructions. These computer program instructions may be provided to a processor of a general purpose computer, special purpose computer, embedded processor or other programmable data processing apparatus to produce a machine, such that the instructions, which execute via the processor of the computer or other programmable data processing apparatus, create means for implementing the functions specified herein.

These computer program instructions may also be stored in a computer-readable memory that can direct a computer or other programmable data processing apparatus to function in a particular manner, such that the instructions stored in the computer-readable memory produce an article of manufacture including instruction means which implement the function specified herein.

The computer program instructions may also be loaded onto a computer-readable or other programmable data processing apparatus to cause a series of operational steps to be performed on the computer or other programmable apparatus to produce a computer implemented process such that the instructions which execute on the computer or other programmable apparatus provide steps for implementing the functions specified herein.

The embodiments and examples described above are illustrative only and it should not be construed in any way that the present invention is limited to these particular embodiments or examples. Thus, various changes and modifications may be effected by one skilled in the art without departing from the spirit or scope of the present invention as defined in the appended claims.

What is claimed:
1. A method of communicating a Heart Rate Variability (HRV) fields of two or more users participating in an on-line collaboration environment via respective client devices over a network via a server device, said method comprising:
 detecting, at a respective client device of a respective user, a Heart Rate Variability (HRV) field emitted by that user at a respective device while the users participating in the on-line collaboration environment;
 recording, at said respective client devices of the users, the Heart Rate Variability (HRV) field of the respective users;
 encoding, at the client devices of the users, the recorded Heart Rate Variability (HRV) field as data;
 transmitting, from the client devices of the users, the encoded HRV field data together with a message to a server device;

receiving, at the server device, the encoded HRV field data with the message;

decoding, at the server device, the encoded HRV field data;

summing, at the server device, each of the decoded HRV field data of the users currently participating in the on-line collaboration environment and encoding the summed HRV field data;

transmitting the encoded summed HRV field data to each user client device in the on-line collaboration environment;

decoding, at the each user client device in the on-line collaboration environment, the transmitted encoded summed HRV field data to obtain the summed HRV field of the two or more users;

displaying, at the each client user device, the message; and simultaneously broadcasting, at the each user client device, the decoded summed HRV field data of the two or more users as an electromagnetic signal for direct application to each user in the on-line collaboration environment to influence a physical state of the each user in the on-line collaboration environment, the simultaneously broadcasting including:

transforming the decoded summed HRV field data to an effect for sensing by the each user in the on-line collaboration environment; and emitting the effect to the each user in the on-line collaboration environment in order for the each user in the on-line collaboration environment to experience the effect.

2. The method of claim 1, further comprising:

associating the encoded summed HRV field data with a symbol indicating a state of common emotion of the each user at a time of the recording said HRV field, the encoded summed HRV field data and the symbol representing the state of the common emotion; and, transmitting the encoded summed HRV field data and said associated symbol together with the message to the each user client device in the on-line collaboration environment, said message and symbol being displayed at said each user client device thereby informing said each user in the on-line collaboration environment about the common emotive state of users in the on-line collaboration environment.

3. The method of claim 2, further comprising:

selecting, by a user in the on-line collaboration environment, via a respective client device, said displayed symbol; and, in response, broadcasting said decoded summed HRV field data for direct application to the each user in the on-line collaboration environment.

4. The method of claim 2, further comprising:

storing in a memory storage device associated with said each user in the on-line collaboration environment, one or more symbol definitions, each respective symbol definition including a different encoded HRV field data corresponding to a respective different physical or an emotional state and a respective different associated symbol; and generating, for said sender, a display interface adapted to indicate said stored symbol definitions configured for selection by a first user in the on-line collaboration environment when generating a message, wherein said transmitted message includes the encoded summed HRV field data and said symbol of the emoticon definition selected by said first user.

5. The method of claim 4, wherein said stored symbol definitions are adapted for reuse by said first user when sending subsequent messages to other users.

6. A system for communicating an electromagnetic signal associated with a Heart Rate Variability (HRV) fields of two or more users participating in an on-line collaboration environment comprising:

client devices associated with the two or more users, each of said client devices comprising at least one medium for embodying machine readable data and machine performable program code; at least one interface for communicating externally; and, at least one processor adapted to perform operations responsive to the medium and interface, the operations comprising:

detecting, using a field monitor at a respective client device of a respective user, a Heart Rate Variability (HRV) field emitted by that user at a respective device while the users participating in the on-line collaboration environment;

recording, at said respective client devices of the users, the Heart Rate Variability (HRV) field of the respective users;

encoding, at the client devices, the recorded Heart Rate Variability (HRV) field as data;

transmitting, from the client devices, the encoded HRV field data together with a message to a server device, said server device associated with the on-line collaboration environment, said server device comprising at least one medium for embodying machine readable data and machine performable program code; at least one interface for communicating externally; and, at least one processor adapted to perform operations responsive to the medium and interface, the operations comprising:

receiving, at the server device, the encoded HRV field data with the message via said at least one interface of said server device;

decoding, at the server device the encoded HRV field data;

summing, at the server device, each of the decoded HRV field data of the users currently participating in the on-line collaboration environment and encoding the summed HRV field data;

transmitting the encoded summed HRV field data to each user client device in the on-line collaboration environment;

the each user client device in the on-line collaboration environment decoding the transmitted encoded summed HRV field data at to obtain the summed HRV field of the two or more users;

the each user client device displaying the message; and simultaneously broadcasting, at the each user client device, the decoded summed HRV field data of the two or more users as an electromagnetic signal for direct application to each user in the on-line collaboration environment to influence a physical state of the each user in the on-line collaboration environment, the simultaneously broadcasting including: transforming the decoded summed HRV field data to an effect for sensing by the each user in the on-line collaboration environment; and emitting the effect to the each user in the on-line collaboration environment in order for the each user in the on-line collaboration environment to experience the effect.

7. The system as claimed in claim 6, wherein said message includes content indicating a current physical status of said sender, said system further comprising:

the each user in the on-line collaboration environment comparing a physical status of the two or more users indicated by the decoded summed HRV field data with a corresponding physical state of the two or more users as experienced by the each user from the applied decoded HRV field data of the broadcast electromagnetic signal, wherein the result of the comparison is indicative of an authenticity of the message.

8. The system of claim 7, wherein said operations performed by said at least one processor of said first communications device comprises:

associating, by one of the two or more users, the encoded summed HRV field data with a symbol indicating a state of common emotion of said each user at a time of the recording said HRV field, the encoded summed HRV field data and the symbol representing the state of the common emotion;

transmitting the encoded summed HRV field data and said associated symbol together with the message to the each user in the on-line collaboration environment, said message and symbol being displayed at said receiver thereby informing said second user about a corresponding emotive state of said sender; and selecting by a user in the on-line collaboration environment, via a respective client device, said displayed symbol; and, in response, broadcasting said decoded summed HRV field data for direct application to the each user in the on-line collaboration environment.

* * * * *